United States Patent [19]

Dolan

[11] 4,129,030
[45] Dec. 12, 1978

[54] SENSING APPARATUS AND METHOD

[75] Inventor: James P. Dolan, Seattle, Wash.

[73] Assignee: ADS Systems, Inc., Seattle, Wash.

[21] Appl. No.: 841,802

[22] Filed: Oct. 13, 1977

[51] Int. Cl.² .......................................... G01N 27/04
[52] U.S. Cl. .................................. 73/23; 340/632
[58] Field of Search ............ 73/23, 27 R; 324/71 SN; 338/13, 27, 34, 35; 340/237 R; 23/232 E, 254 E

[56] References Cited

U.S. PATENT DOCUMENTS

| 3,045,198 | 7/1962 | Dolan et al. | 338/13 |
| 3,247,478 | 4/1966 | Craig | 338/35 |
| 3,507,145 | 4/1970 | Loh | 73/27 R |
| 3,879,985 | 4/1975 | Maslen | 73/27 R |

Primary Examiner—Stephen A. Kreitman
Attorney, Agent, or Firm—Seed, Berry, Vernon & Baynham

[57] ABSTRACT

A sensing apparatus and method, for sensing liquids, vapors and gases, which includes a detection device constructed in accordance with the disclosures contained in U.S. Pat. No. 3,045,198, issued July 17, 1962, to Dolan et al. When the detection device is operated in a current saturated condition it becomes sensitive even to substances having a Van der Waals' "a" constant of nine or less. A change in the level of the current through the detection device occurs upon exposure of the device to the substance being sensed. This current level change is then detected to indicate the presence of the sensed substance. The relatively small current level change through the detection device may be easily discerned despite the fact that the base current is on the order of milliamperes by placing the detection device in a balanced bridge circuit. Further, the bridge circuit enables easy, accurate normalization of the apparatus in a reference environment.

13 Claims, 5 Drawing Figures

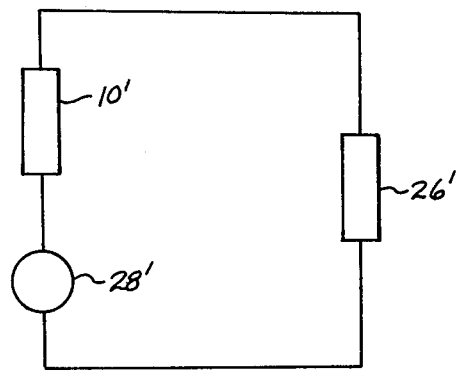
Fig. 3
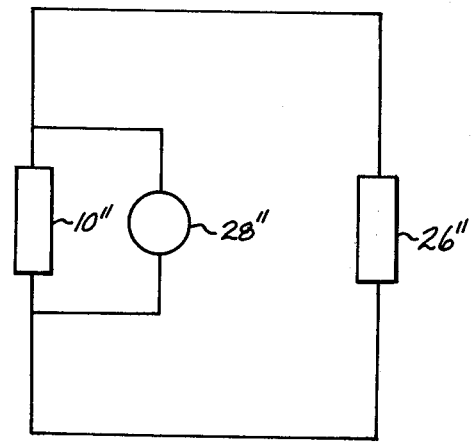
Fig. 4
| VAN DER WAALS' "a" CONSTANT | GAS | CURRENT CHANGE BETWEEN TERMINALS 14, 16 |
|---|---|---|
| 2.25 | METHANE | 310 MICROAMPERES |
| 3.59 | CARBON DIOXIDE | 405 MICROAMPERES |
| 4.39 | ACETYLENE | 625 MICROAMPERES |
| 5.48 | ETHANE | 725 MICROAMPERES |
| 8.66 | PROPANE | 1850 MICROAMPERES |
Fig. 5

SENSING APPARATUS AND METHOD

BACKGROUND OF THE INVENTION

1. Field of the Invention

The sensing apparatus and method of the present invention relate to the art of sensing liquids, vapors and gases. More particularly, the present invention relates to such an apparatus which is electrically actuated and which is responsive to changes in the electrical properties of the current saturated detection device used therein.

2. Description of the Prior Art

It is an increasingly important task in any industrial society to detect the presence of the liquid, vaporous and gaseous phases of many substances. For example, detection may be of consequence since the substance may be intrinsically hazardous due to its explosive, flammable, toxic or noxious character. Obviously, detection is doubly important when such substances enter confined areas where they are unwanted, such as living spaces, mines, bilges, storage tanks, trailers, aircraft and the like.

Detection may also be of import where, although the substance is not particularly perilous in itself, its presence is an indication of some undesirable condition. For example, a fire may be detected by its early products of combustion which, although toxic, may not be as hazardous as the fire itself. Similarly, the presence of a particular substance in the environment surrounding the sensing apparatus may indicate a leak in a supposedly tight system.

One of the many detection devices proposed is disclosed in U.S. Pat. No. 3,045,198, issued July 17, 1962, to Dolan, et al., of which applicant was a joint inventor. Applicant utilizes in his present invention a detection device fabricated in accordance with the disclosures contained in said patent.

In basic form, that patent discloses a detection device which includes a layer of resilient material which is secured to a rigid base member. The active element, a stratum of discrete, electrically conductive, adsorbent particles, adheres to the layer of resilient material, which serves to individually anchor each particle. A pair of spaced-apart electrodes which are in electrical contact with the stratum of conductive, adsorbent particles, completes the detection device. Under reference conditions, as upon exposure to pure atmospheric air, the detection device will normalize and develop a characteristic resistance which is a function of the resistance of the stratum of conductive, adsorbent particles located between the electrodes. However, when the detection device is exposed to the liquid, vapor or gas being sensed, it is found that its resistance changes, usually by increasing.

What is believed to occur is that, in accordance with known principles, minute quantities of the substance being sensed are adsorbed onto the surface of each adsorbent particle, thereby forming a uniform, monomolecular layer which coats the surface thereof. The force of adsorption, known as the Van der Walls' adsorption force, is so great that the layer of adsorbed substance will actually interpose itself between adjacent adsorbent particles which are normally in contact and separate them. As a result, conduction paths established during normalization, when the detection device was exposed to a reference environment, are disrupted, and the characteristic resistance of the detection device is changed, thereby signaling the presence of the sensed substance. As noted in the reference patent, the changed resistance of the detection device is correlated to the Van der Walls' "a" constant; and generally increases as the "a" constant increases.

Of course, the concentration of the sensed substance to which the detection device is exposed has a bearing on the response time of the device; but given sufficient time, even extremely low concentrations of the sensed substance will be noticeably sensed. Upon return of the detection device to the reference environment, the layer of adsorbate gradually dissipates, returning the adsorbent particles to their normal conductive contact, and thus returning the device to its characteristic, normalized resistance.

Through extensive experimental and other use of the detection device disclosed in the reference patent, applicant has discovered that while it was able to detect some substances, it was insensitive to others. Through further study and experimentation, applicant discovered an interesting correlation which gave an indication of being able to predict which substances were detectable by the detection device. Interestingly, Van der Waals' "a" constant seemed to be an indicator and further tests confirmed this hypothesis.

As a result of his experiments, applicant learned that the detection device of the reference patent, when used in accordance with the teachings disclosed therein, was generally sensitive to those substances having a Van der Walls' "a" constant which was greater than about 9, such as gasoline or diesel fuel, for example. However, its lack of sensitivity to certain other substances presented severe limitations on the usefulness of the referenced detection device, inasmuch as a host of common substances have a Van der Walls' "a" constant of about 9 or less. Thus, detection of carbon dioxide, carbon monoxide, propane, acetylene, natural gas and the like, all of which have an "a" constant of 9 or less, was impossible when using the prior art detection device in accordance with the disclosures contained in the reference patent.

Applicant has spent years of research effort in attempting to modify the prior art detection device so that it would be able to detect such substances, since he knew it would be an extremely useful and thus commercially valuable device if it could be so modified. For example, if it were able to detect carbon dioxide and carbon monoxide it could be fabricated as a component in a fire detector and thus be useful to save both life and property. If it were able to detect natural gas, for example, it could be fabricated as a leak detector for such equipment as natural gas pipelines or LNG (liquid natural gas) transport ships. Of course, many other applications for a workable detection device able to sense substances having a Van der Waals' "a" constant of less than 9 are readily apparent to those skilled in the art, and the uses mentioned are only by way of example.

In an effort to improve the prior art detection device and to make it sensitive to substances having a Van der Waals' "a" constant of 9 or less, applicant tried a multitude of approaches. Varying the adsorbent particle size, composition, and mixture did not work. Selection of different materials from which to fabricate the base member and resilient layer did not help. Changing the techniques by which the adsorbent particles were anchored to the resilient layer to thereby alter the depth and security with which each adsorbent particle was anchored also proved fruitless. Modifying the electrodes' composition and configuration proved to be a barren approach. No matter what was tried, applicant was unable to make a detection device that was sensitive to substances having a Van der Waals' "a" constant of less than about 9 when he followed the teachings of the reference patent.

However, through a fortuitous accident when applicant was measuring the current-carrying capabilities of the prior art detection device, he noticed that an anomaly occurred at certain voltage levels. That is, as the voltage across the detection device was increased, the current through the device also increased substantially in accordance with Ohm's Law. However, as the voltage was increased past certain levels, the current rose to a certain value and failed to substantially increase further, a result not predicted by Ohm's Law.

Fortunately, while the device was being operated in this current-saturated condition, i.e., small increases in voltage across the device failed to bring substantially the increases in current through the device as predicted by Ohm's Law; applicant decided to test it to see if it was still able to act as a sensor when operated in this condition. Much to his surprise, he found that the new apparatus was able to detect not only those substances having a Van der Waals' "a" constant of greater than about 9, but it was even able to detect those substances having an "a" constant of about 9 or less. A variety of liquids, vapors and gases were tested, and even helium, with an "a" constant of only 0.03412, was readily detectable. In each case, upon exposure to these substances, an easily detectable current change through the current-saturated detection device occurred that was superimposed on the milliampere order of base current flowing therethrough.

The discovery that the prior art detection device, when operated in a current-saturated condition, was sensitive to even those substances having a Van der Waals' "a" constant of about 9 or less was doubly surprising since one of the prime benefits of the prior art device was that it was a "cold" sensor. That is, because it operated at the ambient temperature and employed no hot elements, it could be safely used to detect even explosive or flammable substances. Its cold operation was the result of the fact that its resistance changed upon exposure to the sensed substance and thus only a few microamperes were needed to detect this resistance change.

Flooding the detection device with current, as applicant now specifies, so that it operates in a current-saturated condition, was not an intuitive step to take for two reasons. First, current saturation is unnecessary when detecting resistance changes in a resistance-type detection device. Secondly, it would be thought that a high current level through the device might raise the temperature of the device to a dangerously hot level or cause ionization of the device which would render it inoperative.

Although applicant is not certain of the exact explanation as to the operation of his current saturated sensing apparatus, he theorizes that when an electrical current of sufficient quantity is caused to pass through the conductive, adsorbent particles of the detection device employed therein, the particles are heated to a temperature just slightly above the temperature of the environment to which the sensing apparatus is exposed. Then, when the current saturated detection device is exposed to a substance with a Van der Waals' "a" constant of about 9 or less, the sensed substance is adsorbed on the adsorbent particles and the heat of adsorbtion thereby released slightly raises the temperature of the particles still further so that a readily detected current change through the device occurs. However, it should be noted that due to its unusual property of becoming current saturated by a mere milliampere order of base current, the detection device is still being operated as a "cold" type sensor, for such a minute current flow causes no substantial heating of the detection device as a whole.

It should be noted that there has been a change in the system of computing the Van der Waals' "a" constant since the referenced patent has issued, as is reflected in the current edition of the *Handbook of Chemistry and Physics*, published by the Chemical Rubber Company of Cleveland, Ohio. Applicant, in the present application, is using the current system.

BRIEF SUMMARY OF THE INVENTION

In basic form, the sensing apparatus for liquids, vapors and gases of the present invention includes a voltage supply means to supply electrical potential across the detection device means sufficient to force the detection device means to operate in a current saturated condition. Indicating means, electrically connected to the detection device means signal the presence of the sensed substance.

Another aspect of the present invention specifies the indicating means to include alarm means to alert the user to the presence of the detected substance.

In another aspect of the present invention, the voltage supply means includes a four terminal bridge-type network wherein the detection device means are across two of the terminals. In addition, the indicating means may be specified to detect the current or voltage changes in the bridge circuit which indicate the presence of the sensed substance.

Other aspects of the present invention specify the detection device means and the voltage supply means to form a simple series circuit, wherein the current changes through the detection device or the voltage changes across it indicate the presence of the sensed substance.

Further aspects of the present invention comprise the method of placing the detection device in a bridge type circuit, applying voltage across the circuit sufficient to force the detection device means to operate in a current saturated condition and using indicating means to detect the current or voltage changes in the bridge circuit which indicate the presence of the sensed substance.

Alternatively, the detection device may be placed in a series circuit with voltage supply means sufficient to force the detection device means to operate in a current saturated condition. Then, indicating means may be electrically connected to the circuit to detect the current or voltage changes therein which indicate the presence of the sensed substance.

It is a primary object of the present invention to provide a sensing apparatus and method which is able to detect substances having a Van der Waals' "a" constant of about 9 or less while still being able to detect substances having an "a" constant of greater than about 9.

It is a further object of the present invention to provide a rugged, simple, easy to fabricate sensing apparatus which is economical, yet durable and reliable in use.

Another object of the present invention is to provide a sensing apparatus which utilizes a detection device which is operated in a current saturated condition to thereby enable it to detect even those substances having a Van der Waals' "a" constant of about 9 or less.

Still another object of the present invention is to provide a "cold" sensing apparatus; that is, one that is able to detect the substances it senses while it operates at substantially the ambient temperature without employing hot elements.

BRIEF DESCRIPTION OF THE DRAWINGS

FIGS. 3 and 4 are simplified schematic diagrams of the present invention utilizing a series type circuit; and FIG. 5 is a tabulation of results obtained utilizing the form of the present invention shown in FIG. 1.

DESCRIPTION OF THE PREFERRED EMBODIMENTS

Figure 1:
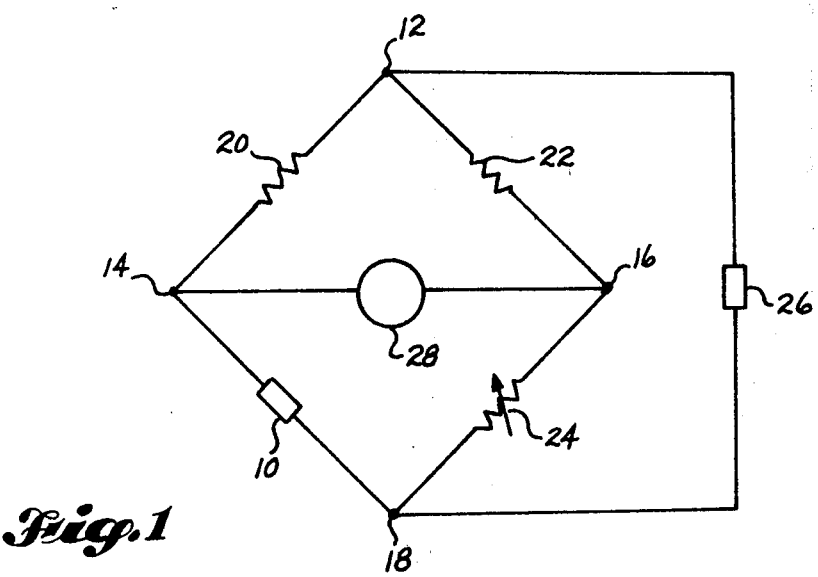
FIG. 1 is a simplified schematic diagram of the present invention utilizing a bridge type circuit.

Turning now to the Figures, it is stressed that the particulars shown are by way of example and for the purposes of illustrative discussion only. They are presented in the cause of providing what is believed to be the most useful and readily understood description of the principles and electrical operation of the present invention. In this regard, it should be emphasized that the schematic diagrams shown in the Figures have been reduced to fundamentals and show no more detail than is required for a basic understanding of the invention and the preferred modes of carrying it out. The description, taken with the drawing, will make it apparent to those skilled in the art how the present invention may be embodied in practice. In particular, the simplified schematics shown in the Figures are not to be taken as a limitation upon the scope of the invention, which is defined by the appended claims forming, along with the Figures, a part of the specification.

Preliminarily, as an aid to an understanding of the present invention, applicant would like to point out that the basic idea involved includes two important concepts. The first concept is that in order for the prior art detection device of U.S. Pat. No. 3,045,198 to be sensitive to those substances having a Van der Waals' "a" constant of about 9 or less, it must be operated in a current saturated condition. As has been explained, the device becomes saturated, and is operated in a current saturated condition, when small increments in the voltage across the detection device do not show the corresponding increases in the current flowing through the device that would otherwise be predicted by Ohm's law, but instead the current flowing through the device remains substantially constant. Thus, all aspects of the present invention require voltage supply means operable to supply voltage across the circuit which includes the detection device, or directly across the detection device itself, sufficient to force the detection device to operate in a current saturated condition. A great number of possible circuits and arrangements of components which will fulfill this requirement will readily occur to those skilled in the art, and it should be repeated that the arrangements shown in the Figures are by merely way of non-limiting example. Of course, applicant does not have the means available to him to make an exhaustive survey of all substances having an "a" constant of about 9 or less to ensure the present invention's sensitivity to all of them, but applicant does indicate that a great many such substances, including those shown in the table illustrated in FIG. 5, are detectable by the sensing apparatus and method of the present invention. In addition, it should be noted that when operated in accordance with the teachings of the present invention the detection device of U.S. Pat. No. 3,045,198 continues to be sensitive to substance having a Van der Waals' "a" constant of greater than 9. Similarly, the present invention is sensitive to the liquid, vaporous and gaseous phases of the substances to which it is sensitive.

The second important concept involves the operating principle inherent in the present invention, which seems to be that when the current saturated detection device is exposed to the sensed substance its electrical properties change and it is this change in the detection device's electrical properties which form the basis by which the presence of the sensed substance may be indicated.

Thus, the present invention includes any electrical arrangement by which the changes, induced by the sensed substance, in the electrical properties of a current saturated detection device are used as the basis for triggering other components to indicate the presence of the sensed substance. Again, a multitude of arrangements utilizing the changing electrical properties of a current saturated detection device will readily occur to those skilled in the art and the simple bridge and series circuits illustrated in FIGS. 1–5 are merely by way of illustrative, non-limiting example.

Turning now to the Figures, we see that FIG. 1 illustrates the sensing apparatus of the present invention as comprising a detection device operated in a current saturated condition while acting as a member in a bridge circuit. The bridge circuit is of conventional design and includes a network having first, second, third and fourth terminals 12, 14, 16 and 18, respectively. A first known resistance 20, a one-half watt 2,000 ohm resistor, is connected across terminals 12, 14; a second known resistance 22, a one-half watt 2,000 ohm resistor, is connected across terminals 12, 16 and a third known resistance 24, a 2,000 ohm variable resistor, is connected across terminals 16, 18. Although only resistance 24 is shown to be variable, it is to be understood that any or all of the known resistances 20, 22, 24 could be made variable. A detection device 10 constructed in accordance with the disclosures contained in U.S. Pat. No. 3,045,198, all of whose disclosures are hereby expressly incorporated by reference, is connected across terminals 14, 18.

By way of nonlimiting example, the detection device 10 comprises an essentially nonconducting base or body in the form of a standard cylindrical one-half watt resistor having a resistance of about 10 million ohms and having a conducting lead at each end. The body of the resistor is then coated with a thin layer of adhesive, such as adhesive type 3145 RTV manufactured by Dow Corning Company. While the adhesive is still tacky, a layer of conductive carbon particles, such as No. 2 powdered flake manufactured by the Joseph Dixon Crucible Co. of Jersey City, N.J., is applied to said body and anchored thereto by said adhesive layer. The detection device 10 is completed by establishing a conductive path between the device's terminals and the conductive particles by means of applying silver paint therebetween. When tested with a standard ohmmeter, the detection device 10 was found to have a resistance of about 900 ohms.

In order to determine at what voltages the detection device 10 became current saturated, the device 10 is placed in a simple series circuit, not illustrated, comprising the device 10, a conventional variable D.C. voltage supply and a conventional milliammeter. As the voltage across the detection device 10 is increased, while the device 10 is exposed to room air for example, corresponding increases in current through the device 10 are observed until at about 10 volts D.C. and higher, the current through the detection device 10 remained substantially constant at about 7.5 milliamperes. Thus at about 10 volts and higher the device 10 was determined to be current saturated since small changes in voltage across the device failed to bring substantially the corresponding current changes through the device 10 which would ordinarily have been predicted by Ohm's Law. Of course, the voltage range at which any particular detection device 10 is current saturated will vary according to the particular construction of the device 10 used.

Referring again now to FIG. 1, voltage supply means 26 are connected across terminals 12, 18 to supply volts 30 D.C. there across to ensure operation of the detection device 10 in a current saturated condition. The polarity of the voltage supply means 26 is not critical. The voltage supply means can be of any conventional design, such as an Eico 1020 power supply, as long as it is operable, when electrically connected across the bridge circuit as illustrated, to supply a potential across the detection device 10 sufficient to force the detection device to operate in a current saturated condition.

Finally, indicating means 28 are connected across terminals 14, 16. The indicating means may comprise any of a variety of equipment which are responsive to either the voltages or currents between terminals 12, 16. Thus, indicating means 28 could be a conventional meter which indicates either the voltage changes across terminals 12, 16 or the current changes flowing therebetween to signal the presence of the sensed substance. Also, the indicating means 28 could be an electrical circuit of any suitable design which is responsive to voltage or current changes between terminals 12, 16 to sound audio, visual or other types of alarm means to signal the presence of the sensed substance. Such a circuit is shown by way of nonlimiting example in FIG. 2.

Figure 2:
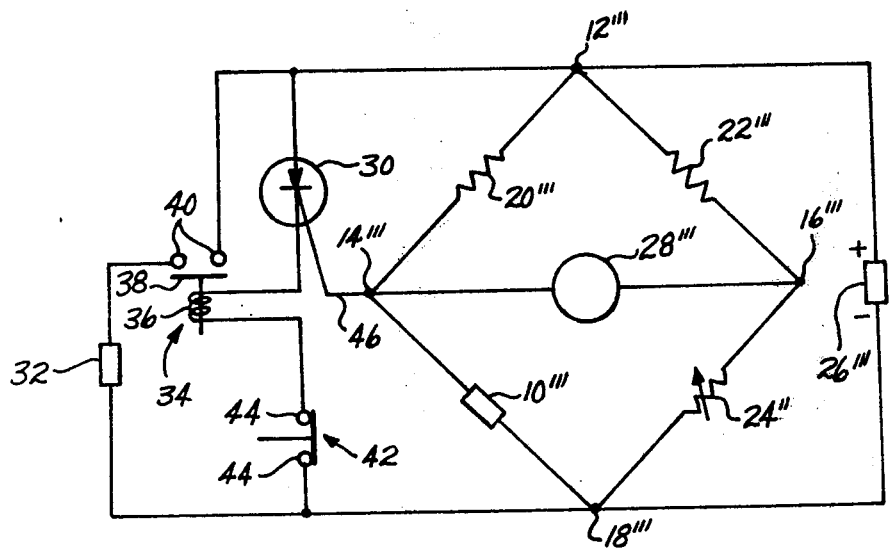
FIG. 2 is a schematic diagram of a simple alarm circuit which may be utilized with the bridge circuit shown in FIG. 1.

Referring now to FIG. 2, we see that it includes a bridge circuit similar to that shown in FIG. 1, with those corresponding elements which are the same as those in FIG. 1 identified by a triple prime in FIG. 2. Voltage supply means 26''' has the polarity shown. Element 30 is an SCR (Silicon Controlled Rectifier) type 3N84 or type T146, element 32 is a Sonalert audio type alarm number SC628 manufactured by the P. R. Mallory Co. of Indianapolis, Indiana, and element 34 is a 600 ohm relay having an actuating coil 36, contactor 38 and output terminals 40. Element 42 is a normally closed reset switch having terminals 44. In use, the bridge portion of the circuit shown in FIG. 2 is operated exactly as the bridge circuit shown in FIG. 1 with the voltage supply means 26''' supplying 30 volts D.C. across terminals 12''', 18''' which is sufficient to cause the detection device 10''' to operate in a current saturated condition. Variable resistor 24''' is adjusted to balance the bridge circuit while the detection device 10''' is exposed to a reference environment, such as room air.

Upon exposure of the detection device 10''' to a substance to which it is sensitive, such as carbon dioxide, its electrical properties change, generally reflected by a decrease in the flow of current therethrough. This causes an unbalance of the bridge circuit which is sensed by the SCR through lead 46, causing the SCR to become conductive and supply current to the actuating coil 36 of the relay 34 causing contactor 38 to close across terminals 40. This supplies power to the audio alarm 32 to signal the presence of the sensed substance. The alarm is silenced by opening switch 42 which cuts off power to the actuating coil 36 of the relay 34, causing the contactor 38 to open, thereby interrupting the supply of power to the alarm 32. Opening of the switch 44 also causes the SCR 30 to cease conducting and upon removal of the detection device 10''' from the presence of the sensed substance for a period of time sufficient to allow the sensed substance to dissipate therefrom, the switch 44 may be closed again without reactivation of the alarm 32, thereby resetting the circuit shown in FIG. 1 for use again.

Returning now to FIG. 1, in operation the sensing apparatus illustrated in FIG. 1 is first exposed to a reference environment, such as pure atmospheric air, while the detection device 10 is forced to operate in a current saturated condition by the voltage supply means 26 which applies 30 volts D.C. across terminals 12, 18. After the detection device has stabilized in the reference environment, one or more of the known resistances, and preferably variable resistor 24, are varied until the voltage across termainals 14, 16, or the current passing between terminals 14, 16 becomes nil as is indicated by the indicating means 28. Now, when the detection device 10 is exposed to the substance it is sensing, its electrical properties change, usually by permitting less current to pass therethrough, thereby causing an imbalance of the bridge circuit which is reflected by current or voltage changes discerned by the indicating means 28 and indicates the presence of the sensed substance. Upon removal of the detection device from the presence of the sensed substance, the device 10 gradually returns to its initial condition.

Tabulated in FIG. 5 are sample test results obtained using the 900 ohm detection device 10 previously described and a Hewlett-Packard 412A VTVM as the detection device 28.

A bridge circuit is preferred for its relatively great sensitivity and ability to detect the electrical changes occurring in the current saturated detection device 10 when it is exposed to the sensed substance, as reflected by the voltage and/or current imbalances caused in the balanced bridge circuit thereby.

Of course, other circuit arrangements are possible such as the simple series circuits illustrated in FIGS. 3 and 4. In FIG. 3, the voltage supply means 26', the detection device 10' and the indicating means 28' are shown in simple series arragnement and are constructed similarly to their corresponding elements which have been described with reference to FIG. 1. Again, the voltage supply means 26' are chosen to be capable of supplying potential across the detection device 10 sufficient to force it to operate in a current saturated condition, say 30 volts. The indicating means 28', such as a milliammeter, here sensitive to changes in current passing through the series circuit, detects the current changes passing through the detection device 10 caused when the detection device is exposed to the sensed substance. Removal of the detection device 10 from the presence of the sensed substance gradually returns the detection device to its initial condition.

Referring now to FIG. 4, the circuit shown therein comprises a simple series connection between the voltage supply means 26" and the detection device 10". Indicating means 28" such as a voltmeter, is connected in parallel across the detection device 10 and is sensitive to the voltage variations across the detection device when the detection device is exposed to the sensed substance. Elements 10" and 26" are constructed similarly to elements 10 and 26 which have been described with reference to FIG. 1. Here again, the voltage supply means 26" are selected to be operable to supply potential across the detection device 10 sufficient to force the detection device 10 to operate in a current saturated condition, say 30 volts. Upon removal of the detection device 10 from the presence of the sensed substance, the detection device gradually returns to its initial condition.

The operation of the circuits shown in FIGS. 3 and 4 are similar, and will be described together. First, the voltage range at which the detection device 10', 10" is current saturated is determined as has been described in reference to detection device 10. Next, the voltage supply means 26', 26" are selected to provide a voltage across the device 10', 10" sufficient to cause it to operate in a current saturated condition, and the device 10', 10" is exposed to a reference environment such as room air and allowed to normalize. Then, when the device 10', 10" is exposed to the sensed substance its electrical properties change, usually reflected by a change in current passing therethrough, which change is reflected by the indicating means 28', 28", to signal the presence of the sensed substance. Upon return of the device 10', 10" to the reference environment, the device soon returns to its initial condition.

From the foregoing, various further applications, modifications, and adaptations of the apparatus disclosed by the foregoing preferred embodiments of the present invention will be apparent to those skilled in the art to which the present invention is addressed, within the scope of the following claims.

Having thus described the invention, what is claimed is:

1. Sensing apparatus for liquids, vapors and gases comprising:
   (a) detection device means of the type comprising a plurality of independently anchored electrically conductive particles, adsorbently sensitive to liquids, vapors or gases, with the particles arranged in sequential contact to form one or more conductive paths between separated points;
   (b) voltage supply means, electrically connected to the detection device means and supplying electrical potential across the detection device means sufficient to cause said detection device means to operate in a current saturated condition; and
   (c) indicating means electrically connected to the detection device means to indicate when the current saturated detection device means are exposed to the substance being sensed.

2. Sensing apparatus according to claim 1, wherein the indicating means further includes alarm means to indicate the presence of the sensed substance.

3. Sensing apparatus according to claim 1, wherein:
   (a) the voltage supply means includes a four terminal bridge network comprising a first known resistance R1 across the first and second terminals, a second known resistance R2 across the first and third terminals and a third known resistance across the third and fourth terminals, at least one of the resistances being variable;
   (b) the detection device means are across the second the fourth terminals;
   (c) the voltage supply means further include means for impressing a potential across the first and fourth terminals; and
   (d) the indicating means are electrically connected across the second and third terminals.

4. Sensing apparatus according to claim 3, wherein the indicating means detect current changes between the second and third terminals.

5. Sensing apparatus according to claim 3, wherein the indicating means detect the voltage changes across the second and third terminals.

6. Sensing apparatus according to claim 1, wherein the detection device means, voltage supply means and indicating means are electrically connected to form a series circuit wherein the indicating means detects the current changes through the series circuit which reveals the presence of the sensed substance.

7. Sensing apparatus according to claim 1, wherein the detection device means and the voltage supply means are electrically connected to form a series circuit, and the indicating means are connected in parallel across the detection device means to detect the voltage changes across the detection device means which reveal the presence of the sensed substance.

8. A method of sensing liquids, vapors and gases which comprises the following steps:
   (a) forming a four terminal electrical network including a first known resistance R1 across the first and second terminals, a second known resistance R2 across the first and third terminals, and a third known resistance R3 across the third and fourth terminals, at least one of the resistances being variable;
   (b) connecting across the second and fourth terminals detection device means of the type comprising a plurality of independently anchored electrically conductive particles, absorbently sensitive to liquids, vapors and gases, with the particles arranged in sequential contact to form one or more conductive paths between separated points;
   (c) impressing a potential across the first and fourth terminals sufficient to force the detection device means to operate in a current saturated condition;
   (d) connecting the indicating means across the second and third terminals; and
   (e) exposing the detection device means sequentially to a reference environment and to a sensed substance.

9. The method of claim 8 which further comprises the step of indicating the change in current between the second and third terminals when the detection device is first exposed to the reference environment and then exposed to the sensed substance.

10. The method of claim 9, which further comprises the step of indicating the change in voltage between the second and third terminals when the detection device is first exposed to the reference environment and then exposed to the sensed substance.

11. The method of sensing liquids, vapors and gases which comprises the following steps in the order named: p1 (a) forming a series circuit with a voltage supply means and a detection device means of the type comprising a plurality of independently anchored electrically conductive particles adsorbently sensitive to liquids, vapors or gases, with the particles arranged in sequential contact to form one or more conductive paths between separated points;
- (b) adjusting the voltage supply means to impress a potential across the detection device means sufficient to operate the detection device means in a current saturated condition;
- (c) electrically connecting indicating means to the series circuit; and
- (d) sequentially exposing the detection device means to a reference environment and to a sensed substance.

12. The method of claim 11 which further comprises the steps of:
- (a) electrically connecting the indicating means in series with the series circuit; and
- (b) indicating the changes in current flowing in the series circuit when the detection device is first exposed to the reference environment and then exposed to the sensed substance.

13. The method of claim 11, which further comprises the steps of:
- (a) electrically connecting the indicating means across the detection device means; and
- (b) indicating the change in voltage across the detection device means when the detection device means is first exposed to the reference environment and then exposed to the sensed substance.

* * * * *